United States Patent
Greinwald et al.

(10) Patent No.: US 10,369,100 B2
(45) Date of Patent: *Aug. 6, 2019

(54) OPTIMIZED PHARMACEUTICAL FORMULATION FOR THE TREATMENT OF INFLAMMATORY CONDITIONS OF THE ESOPHAGUS

(71) Applicant: Dr. Falk Pharma GmbH, Freiburg (DE)

(72) Inventors: Roland Greinwald, Kenzingen (DE); Ralph Mueller, Freiburg (DE); Markus Proels, Freiburg/Breisgau (DE); Rudolf Wilhelm, Bischweier (DE)

(73) Assignee: Dr. Falk Pharma GmbH, Freiburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/833,428

(22) Filed: Dec. 6, 2017

(65) Prior Publication Data

US 2018/0185277 A1    Jul. 5, 2018

Related U.S. Application Data (63) Continuation of application No. 15/107,735, filed as application No. PCT/EP2014/078391 on Dec. 18, 2014, now Pat. No. 9,867,780.

(30) Foreign Application Priority Data

Dec. 23, 2013 (EP) .................................... 13199278

(51) Int. Cl.
*A61K 9/00* (2006.01)
*A61K 9/20* (2006.01)
(Continued)

(52) U.S. Cl.
CPC .......... *A61K 9/0056* (2013.01); *A61K 9/0007* (2013.01); *A61K 9/2013* (2013.01); *A61K 31/58* (2013.01)

(58) Field of Classification Search
None
See application file for complete search history.

(56) References Cited

U.S. PATENT DOCUMENTS 5,320,852 A * 6/1994 Moest ................. A61K 9/2072
424/464
5,401,514 A * 3/1995 Juch ..................... A61K 9/0056
424/440

(Continued)

FOREIGN PATENT DOCUMENTS

EP   0 720 473 B    11/1998
EP   2 151 235 A1   7/2008
(Continued)

OTHER PUBLICATIONS

Karen Dilger et al., "Active Eosinophilic Esophagitis is Associated with Impaired Elimination of Budesonide by Cytochrome P450 3A Enzymes", *Digestion*, (2013), vol. 87, pp. 110-117.

(Continued)

*Primary Examiner* — Aradhana Sasan
(74) *Attorney, Agent, or Firm* — Chalin A. Smith; Smith Patent, LLC (57) ABSTRACT

Disclosed is an optimized pharmaceutical formulation for the treatment of inflammatory conditions of the esophagus. A pharmaceutical formulation in the form of an orodispersible effervescent tablet is stable, easy to produce, and can be used without dissolving same in a liquid. It is not necessary to drink anything with the tablet as this would reduce the time that the budesonide solution remains in the affected regions of the esophagus. The effervescent tablet of the (Continued)

invention surprisingly resulted in an unexpectedly high rate of histological remission in patients with active eosinophilic esophagitis.

23 Claims, 4 Drawing Sheets (51) Int. Cl.
    *A61K 9/46*     (2006.01)
    *A61K 31/58*    (2006.01)

(56) References Cited

U.S. PATENT DOCUMENTS

| | | | |
|---|---|---|---|
| 5,607,697 A | 3/1997 | Akire et al. | 424/495 |
| 5,639,475 A | 6/1997 | Bettman et al. | 424/466 |
| 5,709,886 A | 1/1998 | Bettman et al. | 424/465 |
| 5,807,577 A | 9/1998 | Ouali | 424/466 |
| 5,807,578 A | 9/1998 | Acosta-Cuello et al. | 424/466 |
| 6,641,838 B2 | 11/2003 | Pather et al. | 424/466 |
| 8,580,300 B2 | 11/2013 | Wilhelm et al. | 424/171 |
| 2005/0106237 A1 | 5/2005 | Wuthrich et al. | 424/464 |
| 2006/0013873 A1 | 1/2006 | Yang et al. | |
| 2007/0071817 A1 | 3/2007 | Rau | 424/466 |
| 2007/0191323 A1 | 8/2007 | Hill et al. | 514/171 |
| 2008/0187586 A1 | 8/2008 | Skrtic et al. | |
| 2009/0181099 A1 | 7/2009 | Dohil | 424/489 |
| 2011/0097401 A1 | 4/2011 | Phillips et al. | 424/479 |

FOREIGN PATENT DOCUMENTS

| | | |
|---|---|---|
| WO | WO 2003/080023 | 10/2003 |
| WO | WO 2009/043844 | 4/2009 |

OTHER PUBLICATIONS

Elad, et al., "Budesonide: A Novel Treatment for Oral Chronic Graft Versus Host Disease," Oral Surgery Oral Medicine Oral Pathology Oral Radiology and Endontics, vol. 95 (3), pp. 308-311 (2003).

Spencer, et al., "Budesonide: A Review of its Pharmacological Properties and Therapeutic Efficacy in Inflammatory Bowel Disease," Drugs, ADIS International Ltd., vol. 50 (5), pp. 854-872 (1995).

Magic Mouthwast (Pharmacist's Letter/Prescriber's Letter) Jul. 2007, vol. 293.

\* cited by examiner

Figure 1: Mean Load with Eosinophils in the respective Esophagus Segment

Figure 2: Mean Total Endoscopic Intensity Score

OPTIMIZED PHARMACEUTICAL FORMULATION FOR THE TREATMENT OF INFLAMMATORY CONDITIONS OF THE ESOPHAGUS

PRIORITY

This application is a continuation of U.S. application Ser. No. 15/107,735 filed Jun. 23, 2016, which, in turn, corresponds to the U.S. national phase of International Application No. PCT/EP2014/078391, filed Dec. 18, 2014, which, in turn, claims priority to European Patent Application No. 13.199278.6 filed Dec. 23, 2013, the contents of which are incorporated by reference herein in their entirety.

BACKGROUND OF THE INVENTION

For the treatment of inflammatory processes and conditions of the esophagus, such as for example the eosinophilic esophagitis, there is required a dosage form that upon oral use allows the local availability of the active ingredient budesonide at a sufficiently high concentration at the focus of inflammation. This concept, referred to as esophagus targeting, cannot be realized with an oral application of a simple active ingredient solution, since there is a high risk in that then the active ingredient is rapidly and almost quantitatively swallowed into the stomach. Thus, the aim of the esophagus targeting preferably should be achieved in that it is allowed for the active ingredient to slowly slide along the mucosa of the esophagus associated with a complete wetting of the surface as well as an adhesion of the active ingredient. This type of use selectively brings the active ingredient to the target location. Furthermore, it is to be considered that the therapeutic treatment of the esophagus ideally makes additional specific demands on the dosage form depending on which patient population is to be treated. The present invention is specifically suitable to provide an age-appropriate dosage form that can easily and reliably be used in adult patients and thus, achieves a high compliance of the prescribed daily dose.

Eosinophilic esophagitis is a chronic, inflammatory disease of the esophagus that is accompanied with a hypofunction of the esophagus and is characterized in an infiltration of the esophageal epithelium with eosinophilic granulocytes. Eosinophilic esophagitis was casuistically described since the late 1970s and increasingly diagnosed since the late 1990s. It seems to be present a Th2 cell-mediated response to airborne allergens and allergens taken in by food that results in the incretion of IL-13, IL-5 and subsequently in the increased production of eo-taxin-3. Hereby, eosinophilic granulocytes are attracted. Clinically, an often long-standing dysphagia as well as bolus impactions are of immediate importance. Making a diagnosis according to standard requires the detection of ≥15 eosinophils/high power field in the esophagus in patients having symptoms of a dysfunction of the esophagus. In some patients there are only observed mucosal changes that can easily be overlooked. Eosinophilic esophagitis predominantly affects men and often occurs both in the childhood and the younger adulthood.

WO 2009/064417 discloses compositions for the treatment of gastrointestinal inflammations. The compositions described there comprise a corticosteroid and at least one additional agent for the treatment of the inflammation. In WO 2009/064457 there are disclosed corticosteroid-containing compositions that are suitable for the treatment of inflammations of the gastrointestinal tract.

US 2007/0111978 describes methods of alleviating inflammatory diseases of the gastrointestinal tract. It is suggested the preparation of a highly viscous solution of a budesonide suspension with a very high concentration of sucralose. US 2009/0264392 describes methods and compositions that are suitable for the treatment of eosinophilic esophagitis. In this therapeutic method a steroid and an agent adhering to the mucosa are used.

It is an object of the present invention to provide pharmaceutical formulations that on the one hand involve advantages in application and on the other hand can be easily prepared and provided in a storage-stable form.

SUMMARY OF THE INVENTION

The present invention relates to pharmaceutical formulations, in particular an effervescent tablet for orodispersible use that comprises budesonide or a pharmaceutically acceptable salt or derivative thereof as a pharmaceutical active ingredient and is preferably used in adults for the treatment of inflammatory diseases of the esophagus.

It is generally known to use effervescent tablets that after dissolution in water are used as a drinking or rinse solution. Said use of the active ingredient has various drawbacks for the described indication such as for example the use of an increased volume of water (typically 250 ml) and the associated dilution of the active ingredient or distribution of the active ingredient throughout the oral cavity as well as the commonly practiced fast swallowing of the solution into the stomach. Also known is the use of budesonide in eosinophilic esophagitis (Straumann et al., Gastroenterology, 2010. p. 1526-1537). However, in this study liquid ampoules, so-called "Respules" were used, the normal use of which is inhalation, wherein the content of the ampoule is filled into an atomizer in advance and then, is inhaled. Deviating from the normal use in the cited study the budesonide suspension of the ampoule was used as a drinking solution.

However, the effervescent tablet according to the invention is not diluted in water before use and thus, markedly differentiates from the usual manner of use of the effervescent tablets. The effervescent tablet according to the invention is not used to prepare a drinking solution, but is used orally and for example put on the tongue, preferably the tip of the tongue and slowly dissolves with salivary exposure in the mouth. Thus, the orodispersible effervescent tablet according to the invention differs significantly from the known formulations in view of composition and form.

The orodispersible effervescent tablet according to the invention can also be referred to as lingual effervescent tablet, since during application it should preferably be contacted with the tongue. The formulation form can also be abbreviated as BUL (=budesonide-containing lingual effervescent tablet).

The orodispersible use of the effervescent tablet is a specific use form in which the tablet as such is orally used and for example, is put on the tongue, preferably the tip of the tongue and after the mouth has been closed is slightly pressed against the palate. In this way, the effervescent reaction gets going and the salivation is stimulated within ca. 5-15 seconds. The constituents of the tablet start to dissolve in the saliva. By the natural swallowing reflex then the saliva is swallowed in portions and continuously wets the esophagus, so that in this way there is an adhesion of budesonide to the mucosa. During the dispersal of the effervescent tablet the patient swallows an average of 5-10 times, so that the esophagus is permanently wetted with the active ingredient-containing saliva. The effervescent tablet disintegrates completely and no noticeable fragments are left. Additional drinking of liquid is not necessary, since no stimulus to drink is triggered. That is, an advantage of the optimized formulation is that no additional liquid must be drunk, and thus, a sufficiently long retention time of the therapeutically active substance budesonide in the affected areas of the esophagus is ensured. The use is completed after 1.5 to 2 minutes and allows a concentrated distribution of budesonide on the esophagus. Here, the distribution of the active ingredient within the esophagus on the mucosa of the esophagus exclusively is by saliva. Also, a wide distribution of budesonide already in the oral cavity is avoided. The orodispersible effervescent tablet according to the invention can be taken by the patient very easy at appropriate times.

The orodispersible effervescent tablet according to the invention in use is put into the oral cavity of the patient where it rapidly disintegrates into a plurality of small particles. Advantageously, the orodispersible effervescent tablet according to the invention not only has the ability to rapidly disintegrate in case of a small amount of liquid, i.e. preferably without additionally drinking a liquid. Another advantage is an acceptable taste and a good mouth feel in use. Also of advantage is the sufficient fracture strength and high storage stability even under conditions of a high temperature and high air humidity as well as the possibility of a high loading with the active ingredient budesonide. The orodispersible effervescent tablet according to the invention has a high mechanical stability, which is why further processing, packaging, and transport are no problem. It is particularly noteworthy that the orodispersible effervescent tablets according to the invention have an improved long-term stability compared to the known pharmaceutical formulations, what is demonstrated by tables 2 and 3, for example.

The use of the effervescent tablet according to the invention significantly reduces the risk of an undesired absorption of budesonide into the systemic circle. So, there is no buccal or sublingual use of the dosage form. Moreover, in the normal use no relevant amounts of budesonide are absorbed through the oral mucosa. In contrast to orally disintegrated tablets, that also are orodispersibly used, there is the clear advantage that the dispersal of the effervescent tablets allows a continuous release lasting 1.5 to 2 minutes and thus, a topic application of the active ingredient to the mucosa of the esophagus. However, orally disintegrated tablets for use have the drawback that they immediately disintegrate and therefore, can only be taken in one gulp. Moreover, compared to orally disintegrated tablets effervescent tablets are manufactured industrially much simpler.

Thus, the object of the present invention are orodispersible effervescent tablets containing 0.25 mg to 5 mg of budesonide, preferably 0.3 to 4 mg, more preferably 0.4 to 3 mg, and most preferably 0.5 to 2.0 mg of budesonide. The budesonide used can be used in any pharmaceutically applicable form. The given amount represents the total amount of the active ingredient budesonide in an orodispersible effervescent tablet. In a preferred embodiment the orodispersible effervescent tablet according to the invention does not contain any further pharmaceutical active ingredient.

DETAILED DESCRIPTION OF THE INVENTION

An essential component of the orodispersible effervescent tablet is a system that can generate a gas in the presence of saliva so as to achieve the effervescent effect. It is required that said gas generating system is pharmaceutically acceptable. On the one hand, such a gas generating system is comprised of a weak acid or a salt of a weak acid, respectively. In the presence of water the free weak acid arises from this. However, the acid must not be too strong in order to avoid health problems. This may be tartaric acid, acetic acid, lactic acid, and more preferably citric acid. Usually, the salts of the acids are used, i.e. for example sodium, magnesium, or calcium salts. The other component of the gas generating system is comprised of a salt of an acid that in conjunction with a further acid can release a gas. Preferably, these are salts of the carbonic acid. These may be carbonates or hydrogen carbonates, such as for example sodium or potassium carbonate or sodium or potassium hydrogen carbonates or calcium carbonates as well as mixtures of these salts. It is essential that a gas perfectly safe for health, namely $CO_2$, is released in small amount during use of the effervescent tablet. The gas is released by the interaction of the gas generating components with the saliva.

An orodispersible effervescent tablet according to the invention has a mass that is between 100 mg and 200 mg, preferably the orodispersible effervescent tablets have a mass of 120 mg to 160 mg. Most preferred embodiments of the orodispersible effervescent tablets have a mass of 133 mg to 147 mg.

Also the size of the effervescent tablet according to the invention is essential. Preferably, the effervescent tablets have a diameter between 5 and 10 mm. Preferably, the effervescent tablets are round, although a very round shape being not necessarily required. Deviations from the round shape may also be selected. Preferably, the effervescent tablets are biplane with the diameter preferably being between 6.0 and 8.0 mm, and more preferably between 6.9 and 7.3 mm. The height of the orodispersible effervescent tablet is preferably between 1.5 and 3.0 mm, more preferably between 1.6 and 2.8 mm, and most preferably between 1.8 and 2.6 mm.

As to the mechanical properties of the orodispersible effervescent tablet these are essential. The fracture strength of the effervescent tablet is preferably between a value of 10 and 100 N, more preferably between 20 N and 70 N, and is preferably determined according to the European Pharmacopoeia in accordance with the 2.9.8. monography.

During the test of the mechanical strength of tablets the solid specimen is clamped between two plungers or a plunger and an anvil. Then, a force is applied to the specimen (tablet) and the force required to cause a break in the tablet is determined. Determination of the fracture strength of the orodispersible effervescent tablet according to the invention can be performed for example with fully automatic test devices. For example, such test systems are offered by Pharmatest under the designation WHT 3ME. Of course, equivalent test apparatus can also be used.

The preferable fracture strength on the one hand allows a good and reproducible industrial manufacture, but also a sufficient mechanical stability. According to the invention, the orodispersible effervescent tablets have a friability (abrasion strength) of at most 5%, preferably at most 1%. The friability (abrasion strength) is preferably determined in accordance with the European Pharmacopoeia according to the 2.9.7. monography.

Shape, consistency, and mechanical properties of the orodispersible effervescent tablet are essential, since on the one hand the size and shape allow the continuous and relatively uniform dispersal in the presence of saliva. On the other hand, they allow a sufficient mechanical stability, so that the effervescent tablet in the normal use does not prematurely break into pieces and because of that a use according to the invention is no longer possible. The properties of the orodispersible effervescent tablet have the effect that no foreign-body sensation develops in the mouth and thus, the use is found to be subjectively pleasant by the patient.

The properties of the effervescent tablet described in the particularly preferred embodiment allow the variable single dose administration of budesonide in an amount of preferably 0.5 to 3 mg of budesonide. Here, the amount of active ingredient processed has no effect on the described quality parameters that are relevant for the use, such as size, shape, and mechanical stability. Dividing the tablet is not necessary, rather one tablet corresponds to the dose to be used.

The less the dose of budesonide in the effervescent tablet, the higher the demands on the selection of suitable excipients for ensuring a sufficient long-term stability of the dosage form. Then, an undesired decomposition of the active ingredient would be particularly undesired if low doses are administered, because then the pharmaceutically sufficient amount of the active ingredient would no longer be present in the tablets. Surprisingly, it was shown that the physicochemical stability of budesonide in the effervescent tablet is only allowed by the composition according to the invention. Even if individual excipients are part of the prior art of effervescent tablets, preferably only exactly with the qualitative and quantitative composition according to the invention a long-term stability of the dosage form of up to 36 months for all dosage strengths of a budesonide effervescent tablet for orodispersible use is possible. The effervescent tablets according to the invention can be stored at room temperature.

In a preferred embodiment, an orodispersible effervescent tablet according to the invention contains a polyvinylpyrrolidone. These are polymerization products of the vinylpyrrolidone. The low molecular polyvinylpyrrolidones are hygroscopic, according to the invention it is particularly preferred to use the povidone K25. It is also possible to use derivatives of polyvinylpyrrolidone that are known in this field. The amount of polyvinylpyrrolidone used (for example povidone K25) is preferably 1 to 10, more preferably 1.5 to 3.5% by weight, based on the finished tablet.

It is required for the orodispersible effervescent tablet according to the invention to have a pleasant taste. Thus, in a preferred embodiment there is added a substance that leaves a sweet taste upon dissolution in the mouth. Since the use of sucrose can be detrimental, preferably an alternative sweetener is used. In a preferred embodiment this is sucralose. Sucralose is sucrose with the hydroxyl residues being replaced by chlorine atoms. Compared to sucrose sucralose is significantly sweeter. However, the manufacturing conditions and other constituents of the orodispersible effervescent tablet have to be adjusted such that no dispersal of the sucralose occurs that could lead to undesired discolorations. In the orodispersible effervescent tablet the proportion of sucralose preferably is between 0.1 and 1.0% by weight, more preferably between 0.2 and 0.6% by weight, based on the finished tablet.

A further preferably used constituent of the orodispersible effervescent tablet is docusate sodium. This is a white, wax-like substance that is used as a solubilization and emulsifying agent in particular to the active ingredient budesonide. The amount of docusate sodium preferably is between 0.01 and 0.2% by weight, more preferably 0.02 to 0.15% by weight, based on the finished tablet.

A further preferably used excipient is mannitol. The mannitol used in accordance with the invention in preferred embodiment is a polymorph, crystalline solid. The two most often characterized modifications are β and α mannitol that are also designated as modifications I and II. As further modification there was also described δ mannitol. For the manufacture of the orodispersible effervescent tablets according to the invention the properties of the excipients, particularly that of the mannitol, have to meet special requirements. On the one hand it is required that the powder mixtures during the manufacture have a good flowability, on the other hand an optimum compactness is essential, i.e. the ability to form tablets of high strength with low compacting force. Here, the particle size distribution of the individual mannitol crystals can play a central role. According to the invention there is preferably used an amount of 2.0 to 10.0% by weight, more preferably 4.0 to 7.0% by weight of mannitol, based on the finished tablet.

A further important excipient that is preferably used in accordance with the invention are polyethylene glycols. In a preferred embodiment macrogol 6000 is used in an amount of 1.0 to 10% by weight, preferably 2.0 to 7.0% by weight, based on the finished tablet.

A further preferred excipient component is magnesium stearate that is preferably used in an amount of 0.01 to 0.5% by weight, more preferably in an amount of 0.05 to 0.15% by weight.

The components that achieve the effervescent effect in terms of the weight make up the main part of the orodispersible effervescent tablet. Here, in a preferred embodiment this is a mixture of disodium citrate, monosodium citrate as well as sodium hydrogen carbonate. Said effervescent mixture makes up a proportion of weight of about 70 to 95% by weight, preferably 85 to 92% by weight, based on the finished orodispersible effervescent tablet. It is especially the particle shape of the components of the effervescent mixture that is relevant for the mechanical properties of the orodispersible effervescent tablet. Thus, from the available qualities of the individual components there must be selected those which in cooperation with the other excipients and the pharmaceutically active ingredient budesonide can be compacted such that the properties of the finished orodispersible effervescent tablet, particularly the intended fracture strength and friability, can be achieved.

Of course, all of the components of the orodispersible effervescent tablet must add up to 100% by weight.

The orodispersible effervescent tablet according to the invention preferably can be used for the treatment but also for the prevention of inflammatory conditions of the esophagus. The formulation according to the invention allows a continuous delivery of the active ingredient that is pleasant for the patient and that is relatively uniformly distributed on the esophagus. Thus, the active ingredient budesonide is targetedly and efficiently topically brought to the inflammatory regions of the esophagus. The orodispersible effervescent tablets according to the invention are particularly preferably used for the treatment of eosinophilic esophagitis.

Preferred embodiments of the present invention are explained by the following examples.

EXAMPLE 1

It was surprisingly found that a physicochemical stability of the budesonide effervescent tablets of up to 36 months as well as the quality parameters relevant for the use of the effervescent tablet such as size, shape, and mechanical stability can be achieved by the qualitative and quantitative composition given in table 1.

In table 1, there are given particularly preferred concentration information of the components that are preferably used according to the invention. It has not necessarily fully been complied with the values given in the table. However, the essential components and the ratios of the individual components to each other are decisive for the advantageous properties of the orodispersible budesonide effervescent tablets according to the invention.

TABLE 1

Composition of preferred budesonide effervescent tablets
Composition [mg]

|  | Budesonide 0.5 mg Effervescent tablet | Budesonide 1 mg Effervescent tablet | Budesonide 2 mg Effervescent tablet |
| --- | --- | --- | --- |
| Granulate | | | |
| Budesonide | 0.50 | 1.00 | 2.00 |
| Disodium citrate | 67.00 | 67.00 | 67.00 |
| Monosodium citrate | 15.00 | 15.00 | 15.00 |
| Sodium hydrogen carbonate | 45.00 | 45.00 | 45.00 |
| Povidone K25 | 2.00 | 2.00 | 2.00 |
| Sucralose | 0.30 | 0.30 | 0.30 |
| Docusate sodium | 0.05 | 0.05 | 0.05 |
| Sum | 129.85 | 130.35 | 131.35 |
| Final mixture | | | |
| Mannitol | 5.95 | 5.95 | 5.95 |
| Macrogol 6000 | 5.00 | 5.00 | 5.00 |
| Magnesium stearate | 0.10 | 0.10 | 0.10 |
| Sum | 140.90 | 141.40 | 142.40 |

EXAMPLE 2

The results of the durability tests of budesonide 1 mg effervescent tablets at different storage conditions are summarized in table 2. Compared to the initial values even during the storage under the conditions of loading tests no relevant changes were shown.

TABLE 2

Stability results of budesonide 1 mg effervescent tablets

| | Storage period at 25° C./60% relative humidity in months | | | | | | |
| --- | --- | --- | --- | --- | --- | --- | --- |
| | Initially | 3 | 6 | 9 | 12 | 18 | 24 |
| Fracture strength [N] | 36 | 33 | 35 | 35 | 36 | 36 | 35 |
| Dispersal in water [Minutes] | 1.3 | 1.4 | 1.3 | 1.8 | 1.5 | 1.4 | 2.9 |
| Content of budesonide [%] | 101.4 | 99.5 | 100.0 | 100.7 | 99.5 | 99.9 | 98.0 |
| Sum of total impurities [%] | <0.1 | 0.13 | 0.11 | 0.12 | 0.13 | 0.19 | 0.22 |

| | Storage period at 30° C./65% relative humidity in months | | | | | |
| --- | --- | --- | --- | --- | --- | --- |
| | Initially | 3 | 6 | 9 | 12 | 18 |
| Fracture strength [N] | 36 | 37 | 34 | 36 | 34 | 28 |
| Dispersal in water [Minutes] | 1.3 | 1.7 | 1.5 | 1.7 | 1.7 | 2.9 |
| Content of budesonide [%] | 101.4 | 100.5 | 99.6 | 100.0 | 98.1 | 97.3 |
| Sum of total impurities [%] | <0.1 | 0.13 | 0.12 | 0.15 | 0.18 | 0.40 |

| | Storage period at 40° C./75% relative humidity in months | | | |
| --- | --- | --- | --- | --- |
| | Initially | 1 | 2 | 3 |
| Fracture strength [N] | 36 | 21 | 36 | 38 |
| Dispersal in water [Minutes] | 1.3 | 0.9 | 1.7 | 1.8 |
| Content of budesonide [%] | 101.4 | 100.2 | 100.6 | 99.5 |
| Sum of total impurities [%] | <0.1 | 0.14 | 0.27 | 0.39 |

EXAMPLE 3

Compared to the initial values especially during the storage under the condition of climatic zone II no relevant changes are shown. In contrast, the results of table 3 demonstrated that in case of only a slight deviation from this recipe (e.g. exchange of 0.40 mg sucralose with 1.0 mg aspartame) the long-term stability of the budesonide 1 mg effervescent tablets is no longer given. As the failed attempt reveals impressively, in case of a changed recipe the decomposition of budesonide after equally long storage periods increases by a factor of ca. 7. Since this decomposition turns out even more clearly with dosages of less than 1 mg of budesonide the physicochemical stability of the effervescent tablet is preferably given with the qualitative and quantitative composition given in table 1. With less than 1 mg of budesonide per orodispersible effervescent tablet the instability turns out even more clearly.

TABLE 3

Lacking stability of budesonide 1 mg effervescent tablets with modified composition

| | Storage period at 25° C./60% relative humidity in months | | | | | | |
|---|---|---|---|---|---|---|---|
| | Initially | 3 | 6 | 9 | 12 | 18 | 27 |
| Content of Budesonide [%] | 98.6 | 99.7 | 101.1 | 99.8 | 98.9 | 96.8 | 95.7 |
| Sum of total impurities [%] | <0.1 | 0.31 | 0.66 | 0.86 | 0.81 | 1.05 | 1.63 |

| | Storage period at 30° C./65% relative humidity in months | | | | |
|---|---|---|---|---|---|
| | Initially | 3 | 6 | 9 | 12 |
| Content of Budesonide [%] | 98.6 | 100.1 | 100.4 | 99.4 | 98.2 |
| Sum of total impurities [%] | <0.1 | <0.1 | 0.91 | 1.01 | 1.31 |

In this test, 0.4 mg of sucralose were replaced by 1.0 mg aspartame.

EXAMPLE 4

Clinical Data:

In a 4-arm, double blind, randomized, placebo-controlled phase II multicenter study 2×1 mg/day or 2×2 mg/day of budesonide effervescent tablets were compared with 2×2 mg/day oral viscous budesonide suspension or placebo in the treatment of active eosinophilic esophagitis. Blinding was ensured by using the "Double-Dummy" technique. The aim of the study was to show the superiority of the budesonide formulations over placebo. The first primary partial endpoint of said study was the rate of the histological remission, wherein the eosinophils (eos) of the patients in remission had to attain mean number of <16 eos/mm$^2$ hpf ("high power field", i.e. the visual field in the microscope at a magnitude of 400×) after 2 weeks of treatment. As the second primary partial endpoint the difference in the mean number of eos/mm$^2$ hpf between the beginning of the study and the end of the treatment was measured. Both described efficacy parameters were confirmatively examined in a closed test method to enable a comparison of all three verum groups with the placebo group. The design of the study including the described endpoints is virtually identical to the study described in the publication of Straumann, 2010 loc. cit.

Surprisingly, the results of all three test formulations not only were significantly better than that of the placebo, but also better than that of the budesonide formulation that is described in the work of Straumann et al., 2010 loc. cit., in the dosage of 2×1 mg/day this result is significant.

Table 4 shows the results for the histological remission defined as an average of <16 eos/mm$^2$ hpf. Patients that prematurely left the study without a histological secondary inspection having taken place were analyzed as patients that are not in remission. In a sensitivity analysis only patients were analyzed who had completed the study.

TABLE 4

Histological Remission
Number (%) of patients with histological remission

| | BUU-2/EEA | | | Straumann (2010 loc. cit.) | |
|---|---|---|---|---|---|
| | Budesonide 2 × 1 mg Tablet | Budesonide 2 × 2 mg Tablet | Placebo | Budesonide 2 × 1 mg suspension | Placebo |
| FAS at wk 12** | | | | | |
| (LOCF) ITT | 19/19 (100%) | 18/19 (95%) | 0/19 (0%) | 13/18 (72%) | 2/18 (11%) |
| [95% RCI] | [64.7%; 100%] | [57.6%; 99.5%] | — | NA | — |
| p-value* | <0.0001 | <0.0001 | — | <0.0001 | — |

TABLE 4-continued

Histological Remission
Number (%) of patients with histological remission

| | BUU-2/EEA | | | Straumann (2010 loc. cit.) | |
|---|---|---|---|---|---|
| | Budesonide 2 × 1 mg Tablet | Budesonide 2 × 2 mg Tablet | Placebo | Budesonide 2 × 1 mg suspension | Placebo |
| PP at wk 12** | | | | | |
| (LOCF) ITT | 19/19 (100%) | 17/17 (100%) | 0/17 (0%) | — | — |
| [95% RCI] | [63.1%; 100%] | [61.3%; 100%] | — | — | — |
| p-value* | <0.0001 | <0.0001 | — | — | — | histological Remission defined as <5 eos/hpf (corresponding to <16 eos/mm² hpf)
FAS, Full Analysis Set;
PP, Per Protocol Analysis Set;
RCI, repeated confidence interval (for the difference between verum and placebo)
*for the superiority of verum over placebo
**at wk 12, at 12 weeks Also for the analysis of the co-primary endpoint the superiority over the placebo could be shown (table 5). (The comparison with Straumann is not possible, since this endpoint was not studied in Straumann).

TABLE 5

Difference in the mean number eos/mm² hpf (FAS)

| | Budesonide 1 mg Tablet (n = 19) | Budesonide 2 mg Tablet (n = 19) | Budesonide 2 mg Susp. (n = 19) | Placebo (n = 19) |
|---|---|---|---|---|
| mean (SD) | −119.919 (79.275) | −128.120 (78.457) | −96.665 (124.253) | −7.882 (157.939) |
| n | n = 19 | n = 18 | n = 18 | n = 19 |
| p-value* | 0.0006 | 0.0005 | 0.0041 | — |

*for the superiority of verum over placebo

Additionally, it could be shown for all verum groups that in all esophagus segments the load with eosinophils was almost completely eliminated (in a region of 0.2-2.7 eos/mm² hpf). This result confirms that the pharmaceutical formulation according to the invention esophagus-selectively distributes the active ingredient over the entire esophagus. This is illustrated in FIG. 1.

Figure 1:
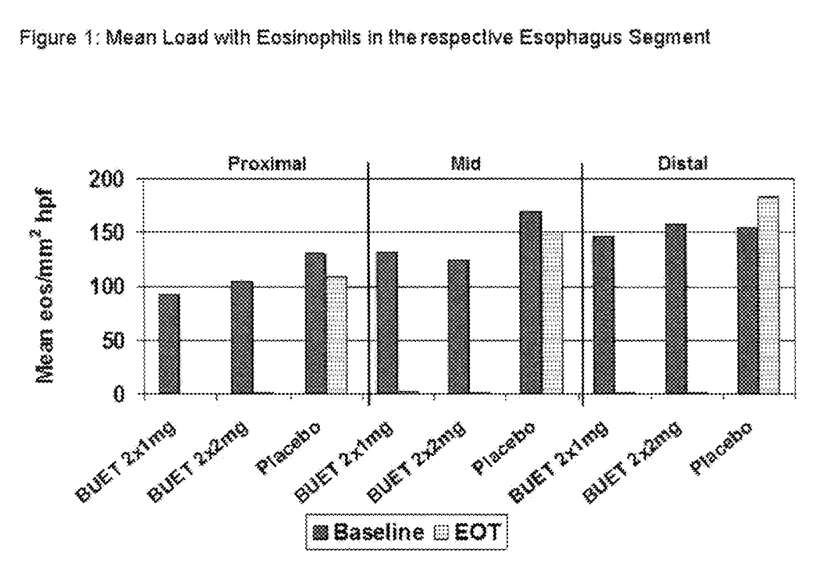
FIG. 1 presents a bar graph depicting the mean load with eosinophils, measured as a mean number of eosinophils/mm$^2$ hpf, in the proximal, the central (Mid) and the distal esophageal segments subsequent to treatment with an orodispersible, budesonide-containing effervescent tablet of the present invention (BUET), either as a twice-daily dose of one tablet with 1 mg of active ingredient (BUET 2×1 mg) or as a twice-daily dose of one tablet with 2 mg of active ingredient (BUET 2×2 mg), as compared to a Placebo.

FIG. 1 shows the mean load with eosinophils in the respective esophagus segment. The esophagus was divided in proximal part, central part (Mid) and the distal part. It was given the mean number of eosinophils/mm² hpf. The abbreviation EOT means "End of Treatment".

EXAMPLE 5

In addition to the described efficacy on the histology it was shown that a 2-week treatment with the formulation according to the invention also results in a statistically significant and clinically relevant improvement of the eosinophilic esophagitis, based on the endoscopic image. This is illustrated in FIG. 2.

Figure 2:
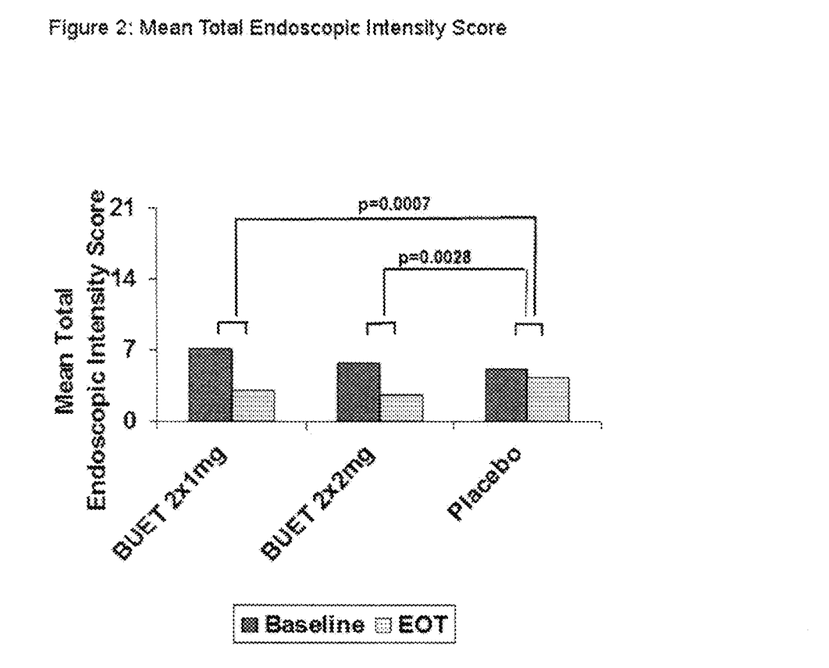
FIG. 2 presents a bar graph depicting the mean total endoscopic intensity score subsequent to the two treatments (BUET 2×1 mg and BUET 2×2 mg) as compared to a Placebo.

In FIG. 2 there is given the mean total endoscopic intensity score. The abbreviation BUET means orodispersible, budesonide-containing effervescent tablet. The abbreviation 2×1 mg means twice-daily dose of one tablet with 1 mg of active ingredient. The abbreviation 2×2 mg means twice-daily dose of an orodispersible effervescent tablet with 2 mg of active ingredient. Baseline means the baseline, EOT means "End of Treatment". Here, Baseline means the first visit of the patient on which the treatment starts and EOT is the last visit during the treatment. Since there is always applied the principle of the LOCF (last observation carried forward) the EOT visit can take place at different times, but always with all test parameters according to the protocol of the last visit of the patients.

EXAMPLE 6

The orodispersible effervescent tablets according to the invention with 2 mg of budesonide per tablet in a study were administered to a group of patients between 20 and 50 years of age. The patients were treated in a test group with one 2 mg budesonide tablet per day. The control group got an orodispersible effervescent tablet without active ingredient (placebo). During a 15-days treatment it was found that the orodispersible budesonide-containing effervescent tablet was well tolerated and that the histological and clinical parameters were significantly improved in contrast to the placebo group. The orodispersible effervescent tablet in view of the applicability by all test persons was entirely evaluated as positive.

EXAMPLE 7

In further examinations, serum/biomarkers for monitoring and checking the response to therapy of a medication of the eosinophilic esophagitis (EoE) were identified. In the clinical study there were included EoE patients who have received a topical steroid therapy (the orodispersible effervescent tablet according to the patent). Various serum markers were tested for their suitability to what extent the response to therapy and the success of the therapy correlate with the changes of these serum markers. The sample material for the serum samples is derived from the clinical study described in the patent application (Example 4).

The "eosinophilic cationic protein, ECP" proved to be particularly suitable as a marker. This is a cytotoxic protein that is released from the granules of activated eosinophilic granulocytes (Rothenberg, Gastroenterology 2009, 1238-1249). It is known that this protein seems to be suitable for monitoring the response of therapy under topical fluticasone (Schlag et al., J Clin Gastroenterol. 2014, 600-606).

Figure 3:
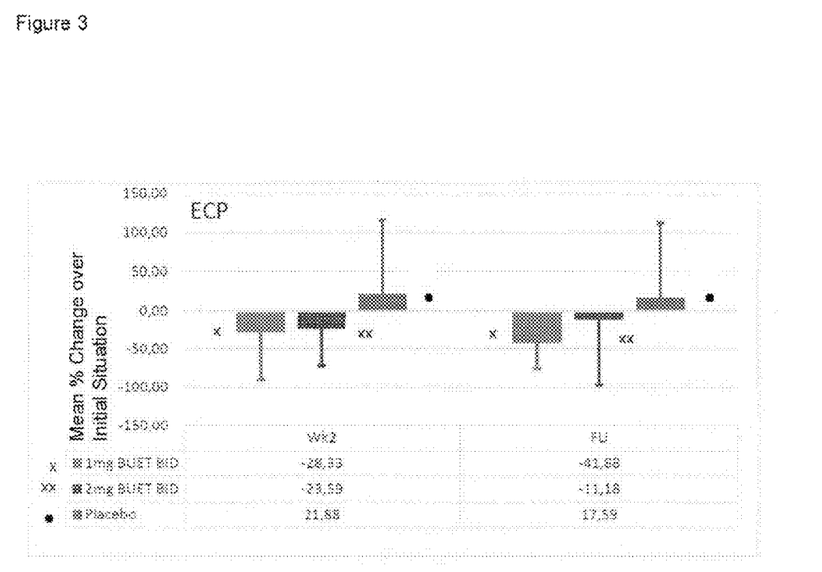
FIG. 3 graphically depicts the long-lasting clinical effect subsequent to the two treatments (BUET 2×1 mg and BUET 2×2 mg) as compared to a Placebo.

It was surprisingly found that ECP not only reflects the clinical results. In addition to the clear correlation between the histological remission and the decrease in the serum level of ECP during the 2-weeks treatment with 1 and 2 mg, respectively, of orodispersible budesonide effervescent tablets there was also shown a lasting therapy success after completion of the 2-weeks treatment. This is illustrated in FIG. 3 (right illustration on "Follow-up Phase, FU"; duration of FU: 2 weeks).

From the experiments performed an additional effect can be deduced. The formulation according to the invention in addition to the effective treatment is also suitable to achieve an ongoing post-treatment clinical effect. It does not come to the frequently observed "rebound effect" when a drug therapy is completed.

EXAMPLE 8

Specification of the Long-lasting Clinical Effect

Figure 4:
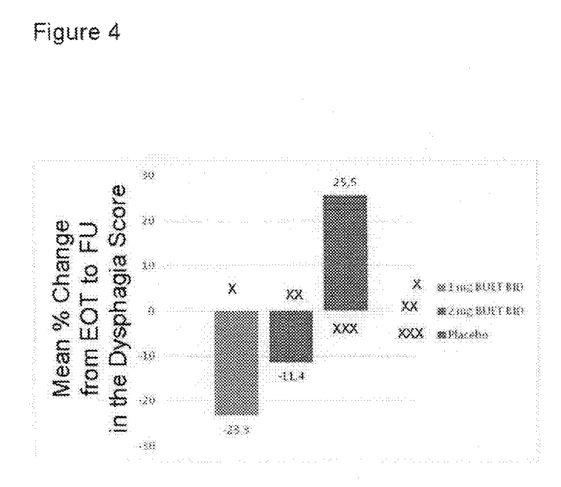
FIG. 4 graphically demonstrate the frequency of dysphagia events subsequent to the two treatments (BUET 2×1 mg and BUET 2×2 mg) as compared to a Placebo.

The long-lasting clinical effect can be shown from additionally performed tests by illustrating the dysphagia score in the treatment-free follow-up period. Said instrument, the so-called "patient reported outcome", demonstrates the frequency of dysphagia events from 0 (no event) to 4 (several events per day) as well as the intensity of these events from 0 (no difficulties in swallowing) to 5 (long-lasting, complete obstruction that requires an endoscopic intervention). The results of the BUU-2 study for this score show that the treatment effect, measured as mean change (in %), lasts between the last treatment and the end of the follow-up period in the verum groups (1 mg and 2 mg of budesonide). In both groups this change is negative, i.e. the score has improved from a higher to a lower value. In the placebo group said value with +25.5% has deteriorated significantly. The results of these tests are summarized in FIG. 4.

What is claimed:
1. An orodispersible effervescent tablet containing:
   a. 0.25 mg to 5 mg of budesonide;
   b. a salt of at least one pharmacologically acceptable acid that, in an aqueous environment, can release a gas with a further acid;
   c. a pharmaceutically acceptable weak acid or salt thereof that decreases the pH value in an aqueous solution; and
   d. 0.1 to 1.0% sucralose;
wherein the effervescent tablet has a mass of 100 mg to 200 mg, a diameter of 5 to 10 mm, and a fracture strength of 10 N to 100 N.
2. The orodispersible effervescent tablet of claim 1, wherein said tablet comprises a lingual effervescent tablet formulated for direct administration to the oral cavity.
3. The orodispersible effervescent tablet of claim 2, wherein said salt of at least one pharmacologically acceptable acid that can release a gas with a further acid is a salt of carbonic acid.
4. The orodispersible effervescent tablet of claim 3, wherein said salt of carbonic acid is selected from the group consisting of carbonates and hydrogen carbonates.
5. The orodispersible effervescent tablet of claim 3, wherein said salt of carbonic acid is selected from the group consisting of $NaHCO_3$, $Na_2CO_3$, $KHCO_3$, $K_2CO_3$, $CaCO_3$ and mixtures thereof.
6. The orodispersible effervescent tablet of claim 2, wherein said pharmaceutically acceptable weak acid or salt thereof that decreases the pH value in an aqueous solution is selected from the group consisting of tartaric acid, acetic acid, lactic acid, and citric acid.
7. The orodispersible effervescent tablet of claim 6, wherein said pharmaceutically acceptable weak acid or salt thereof that decreases the pH value in an aqueous solution is selected from the group consisting of sodium, magnesium, and calcium salts of tartaric acid, acetic acid, lactic acid, or citric acid.
8. The orodispersible effervescent tablet of claim 7, wherein said pharmaceutically acceptable weak acid or salt thereof that decreases the pH value in an aqueous solution is selected from the group consisting of sodium, magnesium, and calcium salts of citric acid.
9. The orodispersible effervescent tablet of claim 8, wherein said pharmaceutically acceptable weak acid or salt thereof that decreases the pH value in an aqueous solution is selected from the group consisting of disodium citrate, monosodium citrate, and mixtures thereof.
10. The orodispersible effervescent tablet according to claim 2, wherein said tablet has a height of 1.5 to 3.0 mm.
11. The orodispersible effervescent tablet according to claim 2, wherein said tablet has a friability of at most 5%.
12. The orodispersible effervescent tablet according to claim 2, wherein said tablet further contains 0.5 to 10% by weight polyvinylpyrrolidone, based on the weight of the finished tablet.
13. The orodispersible effervescent tablet according to claim 2, wherein said tablet further contains 0.01 to 0.2% by weight docusate Na, based on the weight of the finished tablet.
14. The orodispersible effervescent tablet according to claim 1, wherein said tablet further contains 2.0 to 10.0% by weight mannitol, based on the weight of the finished tablet.
15. The orodispersible effervescent tablet according claim 2, wherein said tablet further contains 1.0 to 10.0% by weight macrogol 6000, based on the weight of the finished tablet.
16. The orodispersible effervescent tablet according to claim 2, wherein said tablet further contains 0.05 to 0.5% by weight magnesium stearate, based on the weight of the finished tablet.
17. A method of treating an inflammatory condition of the esophagus, said method comprising the step of administering the orodispersible effervescent tablet according to claim 1 to a patient in need thereof.
18. The method of claim 17, wherein the inflammatory condition of the esophagus being treated is eosinophilic esophagitis.
19. The method of claim 17, wherein said orodispersible effervescent tablet is administered directly to the tongue of the patient and allowed to slowly dissolve with salivary exposure in the mouth.
20. The method of claim 17, wherein said orodispersible effervescent tablet is administered directly to the tip of the tongue of the patient and allowed to slowly dissolve with salivary exposure in the mouth.

21. The method of claim 20, wherein administration of said orodispersible effervescent tablet results in the formation of an adhesion of budesonide to the mucosa, further wherein said adhesion remains in place for a time sufficient to ensure local delivery of a therapeutically effective amount of budesonide to affected areas of the esophagus while avoiding undesired systemic absorption of budesonide.

22. An orodispersible effervescent tablet containing:
    a. 0.25 mg to 5 mg of budesonide;
    b. a salt of at least one pharmacologically acceptable acid that, in an aqueous environment, can release a gas with a further acid;
    c. a pharmaceutically acceptable weak acid or salt thereof that decreases the pH value in an aqueous solution; and
    d. 0.1 to 1.0% sucralose;
wherein:
said tablet comprises a lingual effervescent tablet formulated for direct administration to the oral cavity that has a mass of 100 mg to 200 mg, a diameter of 5 to 10 mm, and a friability of at most 5%.

23. The orodispersible effervescent tablet according to claim 22, wherein said tablet has a fracture strength of 10 N to 100 N.

\* \* \* \* \*